United States Patent [19]

der Avanessian

[11] 4,363,625
[45] Dec. 14, 1982

[54] DENTAL TECHNICIANS TOOL AND TOOL RETAINER

[76] Inventor: Mesrop der Avanessian, 838 Portola, Glendale, Calif. 91206

[21] Appl. No.: 261,125
[22] PCT Filed: Aug. 29, 1980
[86] PCT No.: PCT/US80/01153
  § 371 Date: Aug. 29, 1980
  § 102(e) Date: Aug. 29, 1980
[87] PCT Pub. No.: WO82/00757
  PCT Pub. Date: Mar. 18, 1982
[51] Int. Cl.³ .............................................. A61C 19/00
[52] U.S. Cl. ..................................................... 433/74
[58] Field of Search ................................... 433/74, 53
[56] References Cited

U.S. PATENT DOCUMENTS

| | | | |
|---|---|---|---|
| 1,037,489 | 9/1912 | Kelsey | 433/220 |
| 3,153,283 | 10/1964 | Weissman | 433/74 |
| 3,277,576 | 10/1966 | Kraft | 433/74 |
| 3,470,614 | 10/1969 | Kelly | 433/74 |
| 3,518,761 | 7/1970 | Susman et al. | 433/74 |
| 3,969,820 | 7/1976 | Kulig et al. | 433/74 |
| 4,056,585 | 11/1977 | Waltre | 433/74 |
| 4,205,443 | 6/1980 | Weissman | 433/74 |

Primary Examiner—Gene Mancene
Assistant Examiner—John J. Wilson
Attorney, Agent, or Firm—Wagner & Bachand

[57] ABSTRACT

Dental technician's tool and retainer combination adapted for the rapid and accurate positioning of a tooth model die repetitively on a model base support, the tool comprising an axially elongated member having an upwardly extended head portion engageable with the tooth model die, a downwardly tapered bottom portion and a downwardly diminishing intermediate portion of cusped transverse cross-section, the tool retainer comprising an apertured body having an internal wall defining a tapered bore of cusped transverse cross section adapted to cooperatively seat the elongated member against cocking and rotation, the body being adapted to repetitive insertion in and removal from the model base support, and anchor means on the body periphery adapted to block relative movement of the body and the model base support in projecting member seated relation against cocking or rotation of the tooth die in mounted position on the model base support.

24 Claims, 5 Drawing Figures

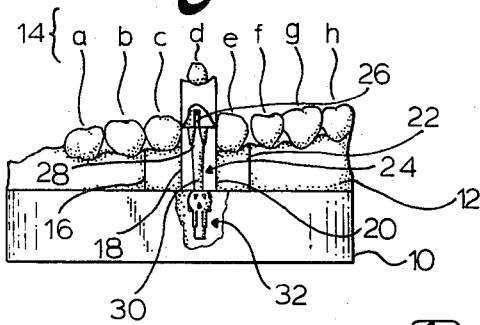
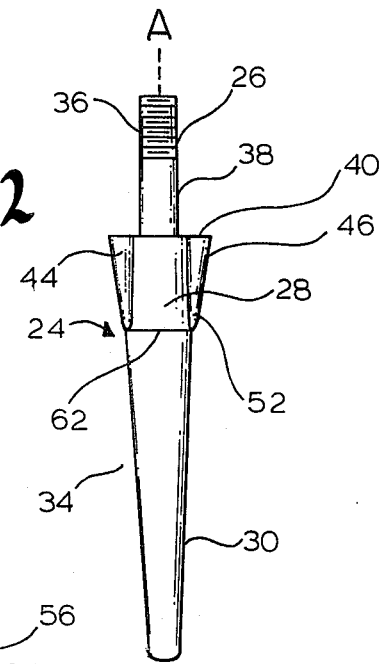
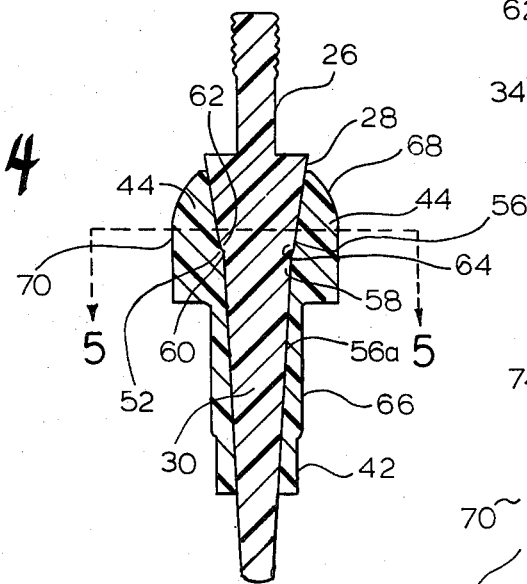
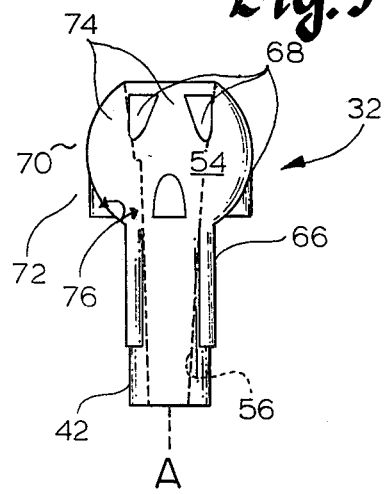
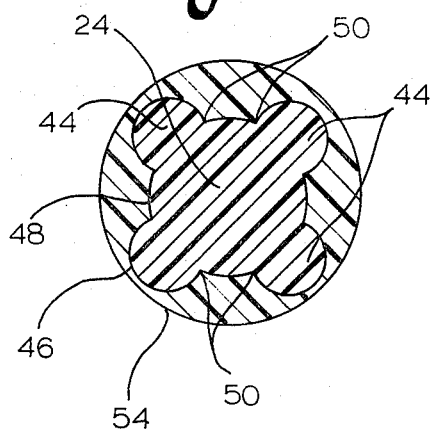

DENTAL TECHNICIANS TOOL AND TOOL RETAINER

TECHNICAL FIELD

This invention has to do with improvements in the tools available to dental technicians as they go about their daily work of creating artificial teeth, crowns and bridges for use in dental restorations. More particularly, the invention has to do with improvements in the pin or dowel tools available to the dental technician to hold tooth dies in precise position for crafting restorative appliances. The invention further relates to retainer devices for such pin or dowel tools, and to novel methods of forming casting cavities by the "lost wax" method using the tool and tool retainers of the invention.

BACKGROUND ART

In the formation of dental restorations, the dentist, prepares the tooth by removing diseased portions, and any other portions needed to mount a replacement surface on the treated tooth. In the case of teeth subjected to root canal treatment, the nerves are removed from the tooth portions deep below the gum line. In other, e.g. crown work, a gold or like material cover is used and is fitted onto the tooth with great precision for reasons of comfort, appearance and disease control. For example, the dentist cuts a "margin" to which the crown is seated exactly. The dental technician receives from the dentist a negative or "impression" of the tooth surface to be restored, and of the adjoining teeth as well. In the dental lab a positive of the tooth area, is prepared using the negative impression as a mold to make a "model". Certain of the teeth for which crowns are to be made for example are required as well. Others have proposed use of two dowel pins on a common base, which blocks rotation but is deficient in cocking resistance in other than the transverse direction. Also the great size of such pin arrangements prohibits their use where very small teeth are involved.

DESCRIPTION OF THE INVENTION

It is accordingly an object of the present invention to provide an improved dental technicians's tool, particularly for the locating of tooth dies in place on a model base support, and further to provide a separately formed retainer for the tool which will not wear loose in use, and which can be color coded, unlike metal dowels, for matching tooth dies to tool retainers remaining on the base support. It is a further object to provide a system for rapidly and securely mounting tooth dies to a base support with self-wedging action downwardly and circularly of the tool and retainer assembly. It is another object to provide novel structures useful as tool and tool retainers and as aids in the generation of crown posts and casting reservoirs, respectively, as well. A still further object is to provide devices formed in plastic for lower cost, color coding, and ease of slip-fit in assembly.

These and other objects of the invention to become apparent hereinafter are realized by the provision, in accordance with the invention, of a dental technician's tool adapted for the rapid and accurate positioning of a tooth model die repetitively on a model base support, the tool comprising an axially elongated member having an upwardly extended head portion engageable with said tooth model die, a downwardly tapered bottom portion receivable in the base support, and a downwardly diminishing intermediate portion of cusped transverse cross-section arranged to engage the base support above the member bottom against cocking or rotation of the tooth die in mounted position on the model base support, but in repetitively vertically separable relation. Preferably, the member head portion is generally cylindrical about the member axis and rises from a transverse shoulder formed on the member; the bottom portion is coaxial with the head portion and tapered at a first angle relative to the member axis; the intermediate portion is frusto-conically tapered downwardly from the transverse shoulder at a second larger angle relative to the member axis and vertically defines a plurality of circumferentially spaced surface rounded splines disposed at a third still larger angle relative to the member axis for spline differential taper regression vertically into the intermediate portion in inwardly tapered cusp-forming relation along the length of the intermediate portion. Also, the member head portion is partially threaded for wet or dry process tooth model die engagement. Further, typically the intermediate portion splines are equidistantly spaced and the member shoulder defines a circular series of lobes coincident with the upper terminus of the splines, the head portion being of reduced diameter relative to the intermediate portion, and the member is comprised of highly rigid, molded, filler.

As mentioned, there is also provided for combination with the dental technician's tool in which the member is a male member, a complementary female member defining a socket adapted to receive the tool in retaining relation on a model base support, specifically a dental technician's tool retainer adapted for the repetitive, rapid and accurate positioning of a tooth model die having an axially elongated member, such as the aforedescribed tool member, projecting fixedly therefrom on a model base support, the tool retainer comprising an apertured body having an internal wall defining a bore adapted to cooperatively seat the elongated member against cocking and rotation, the body being adapted to insertion in a model base support, and anchor means on the body periphery adapted to block relative movement of the body and the model base support in projecting member seated relation. Preferably, the apertured body is a toroidal member, and further includes a series of bosses raised on the toroidal member surface in anchor means defining relation. Typically, the boss series comprise relatively vertically spaced circular series of bosses in angularly indexed relation between series. Preferably, the tool retainer also includes a depending annular skirt extension of the toroidal member wall adapted to insertion in the model base support vertically beyond the toroidal member against cocking of the toroidal member relative to the surrounding model base support, the skirt extension further having a noncircular cross section against rotation about the toroidal member axis of revolution relative to the surrounding model base support, e.g. circumferentially spaced vertical ribs imparting external noncircularity to the skirt extension. In a particular embodiment having the relatively vertically spaced circular series of bosses in angularly indexed relation between series on the toroidal member surface in anchor means defining relation, individual ones of the skirt extension ribs will extend in common vertical planes with one or another of the series of bosses. Like the tool with which it cooperates, the technician's tool retainer may be comprised of molded, highly rigid, filler reinforced plastic.

Accordingly, the invention provides a dental technician's tool and retainer combination adapted for the rapid and accurate positioning of a tooth model die repetitively on a model base support, the tool comprising an axially elongated member having an upwardly extended head portion engageable with the tooth model die, a downwardly tapered bottom portion and a downwardly diminishing intermediate portion of cusped transverse cross-section, the tool retainer comprising an apertured body having an internal wall defining a tapered bore of cusped transverse cross section adapted to cooperatively seat the elongated member against cocking and rotation, the body being adapted to repetitive insertion in and removal from the model base support, and anchor means on the body periphery adapted to block relative movement of the body and the model base support in projecting member seated relation against cocking or rotation of the tooth die in mounted position on the model base support. As noted, the dental technician's tool and tool retainer combination may define a color matchable set in tooth model die base support accurate repositioning facilitating relation.

Other features of the combination are like those of the individual elements and include the apertured body being a toroidal member, the member head portion being generally cylindrical about the member axis and rising from a transverse shoulder formed on the member; the bottom portion being coaxial with the head portion and tapered at an angle relative to the member axis; the intermediate portion is frusto-conically tapered downwardly from the transverse shoulder at a like angle relative to the member axis and vertically defining a plurality of circumferentially spaced surface rounded splines disposed at a relatively large angle relative to the member axis for spline differential taper regression vertically into the intermediate portion in inwardly tapered cusp-forming relation along the length of the intermediate portion; a series of bosses raised on the toroidal member surface in anchor means defining relation, the member head portion being partially threaded for wet or dry process tooth model die engagement, the boss series comprising relatively vertically spaced circular series of bosses in angularly indexed relation between series, the tool intermediate portion splines being equidistantly spaced and the member shoulder defining a circular series of lobes coincident with the upper terminus of the splines; a depending annular skirt extension of the toroidal member wall adapted to insertion in the model base support vertically beyond the toroidal member against cocking of the toroidal member relative to the surrounding model base support, the skirt extension further having a noncircular cross section against rotation about the toroidal member axis of revolution relative to the surrounding model base support; circumferentially spaced vertical ribs imparting external noncircularity to the skirt extension, and the relatively vertically spaced circular series of bosses in angularly indexed relation between series on the toroidal member surface in anchor means defining relation, individual ones of the skirt extension ribs extending in common vertical planes with one or another of the series of bosses, as well as the tool and tool retainer each being comprised of molded, highly rigid, glass fiber filler reinforced nylon.

In its method aspects, the invention contemplates in the method of fabricating restorative crowns having a crown post by forming a suitably shaped cavity at low temperatures around a heat meltable form, melting the form to empty the cavity, and casting the crown forming material thereinto, the cavity including a post defining elongated zone, the improvement comprising using the dental technician's tool hereindefined as the meltable form about which post defining elongated zone is formed; and further as aspects of method, in the method of fabricating tooth restorations by forming a suitably shaped cavity at the terminus of an inlet passage defined by a heat meltable form, the passage having an intermediate enlargement adapted to provide a reservoir of casting material beyond the cavity, the improvement comprising using the dental technician's tool retainer hereindefined as the heat meltable form about which the reservoir enlargement and an adjacent portion of the inlet passage is formed.

THE DRAWINGS

FIG. 1 is a front elevation view of a tooth model on a base support, one tooth die being shown removed;

FIG. 2 is a front elevation view of the dental technician's tool according to the invention;

FIG. 3 is a like view of the tool retainer thereof;

FIG. 4 is a vertical section of the tool and retainer assembled; and,

FIG. 5 is a transverse sectional view of the assembled tool and retainer, taken on line 5—5 in FIG. 4.

PREFERRED MODE

With reference now to the drawings, in FIG. 1 a base support 10 of a rigid "stone" composition has been adhesively attached to the tooth model 12 by pressing the tooth model against the support material while the latter is formable, and thereafter the base support has been trimmed to a convenient size and shape as shown. The tooth model 12 is a positive replication of a number of teeth in the form of dies 14 which are individually labeled a through h. Tooth dies are used to shape crowns, bridges and like appliances. Each tooth die is cut from the model by sawing between the adjacent teeth, note kerfs 16, 18, 20 and 22, indicating that tooth dies c, d, and e have been freed from the model. Die d is shown raised up to illustrate the use of the tool and tool retainer dowel pin assembly of the invention. Inspection of FIG. 1 shows that tool 24 extends upward into die d with head portion 26, and downward toward base support 10 with tool intermediate portion 28 and bottom portion 30, to be received by the tool retainer 32 embedded in the base support.

In dental laboratory practice, the tooth die is removed for work, and reinserted numerous times, and it must be carefully registered in place each time so that refinement of shape can be advanced consistently. In addition to perfect registration, secure mounting with no rotation about the dowel pin axis, and no angular movement, such as rocking in any direction, is essential. Cylindrical or tapered dowel pins permit rotation and misalignment of the tooth die, and without a retainer the problem is aggravated by the wear which may occur in the receiving hole with continued use. The absence of tongue and groove forms on the base support and model is to be noted; these structures are not necessary where the present invention is used.

The present tool and tool retainer solve the problem of rocking and pivoting and accurate registration as well. With reference now to FIGS. 2 through 5, particularly, the unusual shape of the tool 24, and complementary unusual shape of the retainer 32 will become apparent. Initially with reference to the tool 24, it is shown to comprise an axially elongated member 34 having an upwardly extended, generally cylindrical head portion 26, partially threaded at 36 to accommodate wet process or in situ formation of the model around the head, and partially smooth walled, at 38, for dry process drilling and insertion of the head in the model 12. The head portion 26 rises from member transverse shoulder 40 and is substantially reduced in diameter from the shoulder as shown to adequately seat the tooth die and to accommodate various tooth sizes. The tool member 34 below the shoulder 40 has an intermediate portion 28 of downwardly diminishing dimension, and more particularly of a frusto-conical shape to taper downwardly along its length. See FIG. 4 particularly. The member 34 further has a bottom portion 30 which is also downwardly tapered. It is to be noted that the taper of the bottom portion 30 relative to the longitudinal axis A—A of the tool 24 and retainer 32 is at a first angle of approximately 3°; the intermediate portion 28 is also at an angle to the axis A—A of approximately 3°.

Again with reference to the intermediate portion 28, this portion defines four circumferentially spaced splines 44 which are equidistantly spaced and terminate upwardly at the shoulder 40. The splines 44 are at an angle relative to the axis A—A of approximately 36°. The splines further are rounded at the outermost surfaces 46, giving rise, where the spline surfaces meet the wall 48 of the intermediate portion to cusps 50, the spline cross-section itself also defining a cusp where the radius of curvature is sufficiently small, e.g. at 52. The provision of these cusps in the cross-section of the tool is a signal feature of the invention enabling the positive anti-rotation locking characteristic of the present apparatus, and which in combination with the wedge forces generated by the frusto-conical shape of the intermediate portion, ensures accurate registration for the tooth die held by the tool and retainer. The use of multiple angles, in the bottom portion, in the intermediate portion and in the splines on the intermediate portion gives an interlocking effect not heretofore obtained in tooth die pin devices. It can be seen that the cusps 50, 52 by their shape actually interlock against rotation and do not rely solely on friction effects, but provide positive locking action. See FIG. 5, particularly.

The retainer 32 is an apertured body, preferably exteriorly rounded to form a toroidal member 54, having an internal wall 58, stepped at 60 which defines a bore 56 adapted to cooperatively seat the elongated member 34 against cocking and rotation. Elongated member 34 defines an annular shoulder 62 at the base of member intermediate portion 28, which shoulder delimits the frusto-conical intermediate portion 28 downwardly and which together with surface 64 of the intermediate portion provides a complementary surface to bore defining wall 58 adapted to congruently interfit with the bore in wedged relation against cocking of the member 34 relative to the retainer toroidal body member 54. The retainer toroidal member 54 is provided with annular skirt extension 42 to further interfit with and enclose the member 34 against cocking. The skirt extension 42 itself is provided with external radially directed ribs 66 circularly spaced about the extension perimeter in a manner to provide overall a noncircular cross-section to the skirt extension thus to block rotation of the skirt extension and integrally formed body member 54 about the member 54 axis of revolution A—A, in embedded condition in the base support 10.

Provision is also made to anchor the retainer 32 to the base support 10 at the body member 54 so that the retainer holding the member 34 against cocking does not itself shift position. As best shown in FIGS. 3 and 4, anchor means in the form of outwardly, radially projecting tabs or bosses 68 are provided on the upper and lower hemispheres 70 and 72, respectively, of the retainer member 54 in angularly displaced or indexed circumferential series 74 and 76, respectively.

The retainer 32 and tool 24 are preferably molded in high modulus plastic such as glass fiber filled nylon (polyamide resin). Other plastics, particularly the engineering plastics such as polysulfones, polyoxymethylenes, polyhydroxyethers, polyimides and the like may be used, suitably with reinforcing fillers such as glass and carbon black among others. Crosslinking polyolefins and thermosets may also be used as the materials of fabrication. Injection molding is presently the fabrication method of choice, because the tool and retainer lend themselves to inexpensive mass production in this manner. In this connection, economies in production and improved product performance are achieved by using designs in which, as shown in the drawing, the molded in features are designed for most efficient molding, e.g. the ribs 66 are in a common vertical plane with the upper series 74 of bosses 68.

The just described tool finds further utility in the formation of crown posts, those tapered extensions of crowns which interfit the drilled out nerve canals in root canal dentistry. In the past the formation of suitably shaped posts has been handicapped by the extreme thinness of the cross-section and the lack of sufficient strength in the thin cross section wax normally used to define the post, although the crown can be successfully made with the wax. In the procedure known as the lost wax process, the form to be cast in gold, for example, is executed in wax, a vitreous material is poured around the wax and allowed to harden. Upon heating, the wax melts and runs out, leaving a precisely shaped cavity. With the tool of this invention, wax is used to define the crown, but the tool 24, shaped as necessary to meet canal size and taper requirements, is substituted for the wax in the region of the crown post and the vitreous material formed therearound, the tool strength enabling effective forming of the post shape needed. Being preferably thermoplastic, the tool 24 melts and runs out upon heating leaving a post forming cavity.

The tool retainer is similarly useful elsewhere in the dental laboratory, namely in forming the reservoir cavity normally provided, again by the lost wax process just beyond the cavity defining the crown so that an excess amount of casting material will be available and voids prevented in the cast parts. In this use, the retainer 32 is used in replacement of the wax or other expedient in the region between the cast crown or the like and the reservoir area so that the toroidal member 54 shapes a reservoir cavity upon surrounding the wax form and retainer assembly with vitreous material.

I claim:

1. Dental technician's tool adapted for the rapid and accurate positioning of a tooth model die repetitively on a model base support, comprising an axially elongated member having an upwardly extended head portion engageable with said tooth model die, a downwardly tapered bottom portion receivable in said base support, and a downwardly diminishing intermediate portion of cusped transverse cross-section arranged to engage said base support above the member bottom against cocking or rotation of said tooth die in mounted position on said model base support, but in repetitively vertically separable relation, said member head portion being generally cylindrical about the member axis and rising from a transverse shoulder formed on said member; said bottom portion being coaxial with said head portion and tapered at a first angle relative to the member axis; said intermediate portion being frusto-conically tapered downwardly from said transverse shoulder at a second larger angle relative to said member axis and vertically defines a plurality of circumferentially spaced surface rounded splines disposed at a third still larger angle relative to said member axis for spline differential taper regression vertically into said intermediate portion in inwardly tapered cusp-forming relation along the length of said intermediate portion.

2. Dental technician's tool according to claim 1, in which said member head portion is partially threaded for wet or dry process tooth model die engagement.

3. Dental technician's tool according to claim 1, in which said intermediate portion splines are equidistantly spaced and said member shoulder defines a circular series of lobes coincident with the upper terminus of said splines, said head portion being of reduced diameter relative to said intermediate portion.

4. Dental technician's tool according to claim 1, in which said member is comprised of highly rigid, molded, filler reinforced plastic.

5. Dental technician's tool according to claim 1, in which said member is a male member, in combination with a complementary female member defining a socket adapted to receive said tool in retaining relation on a model base support.

6. Dental technician's tool adapted for the rapid and accurate positioning of a tooth model die repetitively on a model base support, comprising an axially elongated member having an upwardly extended head portion engageable with said tooth model die, a downwardly tapered bottom portion receivable in said base support, and a downwardly diminishing intermediate portion of cusped transverse cross-section arranged to engage said base support above the member bottom against cocking or rotation of said tooth die in mounted position on said model base support, but in repetitively vertically separable relation in which said member head portion is generally cylindrical about the member axis and rises from a transverse shoulder formed on said member; said bottom portion being coaxial with said head portion and tapered at a first angle relative to the member axis; said intermediate portion being frusto-conically tapered downwardly from said transverse shoulder at a second larger angle relative to said member axis and vertically defining a plurality of circumferentially spaced surface rounded splines disposed at a third still larger angle relative to said member axis for spline differential taper regression vertically into said intermediate portion in inwardly tapered cusp-forming relation along the length of said intermediate portion, said elongated member being in combination with a dental technician's tool retainer adapted for the repetitive, rapid and accurate positioning of said tooth model die having said axially elongated member projecting fixedly therefrom on a model base support, said tool retainer comprising an apertured body having an internal wall defining a bore adapted to cooperatively seat said elongated member against cocking and rotation, said body being adapted to insertion in a model base support, and anchor means on the body periphery adapted to block relative movement of said body and said model base support in projecting member seated relation.

7. Dental technician's tool retainer according to claim 6, in which said apertured body is a toroidal member.

8. Dental technician's tool retainer according to claim 7, including also a series of bosses raised on the toroidal member surface in anchor means defining relation.

9. Dental technician's tool retainer according to claim 8, in which said boss series comprises relatively vertically spaced circular series of bosses in angularly indexed relation between series.

10. Dental technician's tool retainer according to claim 7, including also a depending annular skirt extension of said toroidal member wall adapted to insertion in said model base support vertically beyond said toroidal member against cocking of said toroidal member relative to the surrounding model base support, said skirt extension further having a noncircular cross section against rotation about the toroidal member axis of revolution relative to the surrounding model base support.

11. Dental technicians tool retainer according to claim 10, including also circumferentially spaced vertical ribs imparting external noncircularity to said skirt extension.

12. Dental technician's tool retainer according to claim 11, including also relatively vertically spaced circular series of bosses in angularly indexed relation between series on said toroidal member surface in anchor means defining relation, individual ones of said skirt extension ribs extending in common vertical planes with one or another of said series of bosses.

13. Dental technician's tool retainer according to claim 6, in which said retainer is comprised of molded, highly rigid, filler reinforced plastic.

14. Dental technician's tool and retainer combination adapted for the rapid and accurate positioning of a tooth model die repetitively on a model base support, said tool comprising an axially elongated member having an upwardly extended head portion engageable with said tooth model die, a downwardly tapered bottom portion and a downwardly diminishing intermediate portion of cusped transverse cross-section; said tool retainer comprising an apertured body having an internal wall defining a tapered bore of cusped transverse cross-section adapted to cooperatively seat said elongated member against cocking and rotation, said body being adapted to repetitive insertion in and removal from said model base support, and anchor means on the body periphery adapted to block relative movement of said body and said model base supports in projecting member seated relation against cocking or rotation of said tooth die in mounted position on said model base support; said tool and retainer defining a color matchable set in tooth model die base support accurate repositioning facilitating relation.

15. Dental technician's tool and tool retainer combination according to claim 14, in which said apertured body is a toroidal member.

16. Dental technician's tool and tool retainer combination according to claim 14, in which said member head portion is generally cylindrical about the member axis and rises from a transverse shoulder formed on said member; said bottom portion is coaxial with said head portion and tapered at a first angle relative to the member axis; said intermediate portion is frusto-conically tapered downwardly from said transverse shoulder at a like angle relative to said member axis and vertically defines a plurality of circumferentially spaced surface rounded splines disposed at a relatively large angle to the member axis for spline differential taper regression vertically into said intermediate portion in inwardly tapered cusp-forming relation along the length of said intermediate portion.

17. Dental technician's tool and tool retainer combination according to claim 16, including also a series of bosses raised on the toroidal member surface in anchor means defining relation.

18. Dental technician's tool and tool retainer combination according to claim 17, in which said member head portion is partially threaded for wet or dry process tooth model die engagement.

19. Dental technician's tool and tool retainer combination according to claim 18, in which said boss series comprise relatively vertically spaced circular series of bosses in angularly indexed relation between series.

20. Dental technician's tool and tool retainer combination according to claim 18, in which said tool intermediate portion splines are equidistantly spaced and said member shoulder defines a circular series of lobes coincident with the upper terminus of said splines.

21. Dental technician's tool and tool retainer combination according to claim 18, including also a depending annular skirt extension of said toroidal member wall adapted to insertion in said model base support vertically beyond said toroidal member against cocking of said toroidal member relative to the surrounding model base support, said skirt extension further having a noncircular cross section against rotation about the toroidal member axis of revolution relative to the surrounding model base support.

22. Dental technician's tool and tool retainer combination according to claim 21, including also circumferentially spaced vertical ribs imparting external noncircularity to said skirt extension.

23. Dental technician's tool and tool retainer combination according to claim 22, including also relatively vertically spaced circular series of bosses in angularly indexed relation between series on said toroidal member surface in anchor means defining relation, individual ones of said skirt extension ribs extending in common vertical planes with one or another of said series of bosses.

24. Dental technician's tool and tool retainer combination according to claim 23, in which said tool and tool retainer are each comprised of molded, highly rigid, glass fiber filler reinforced nylon.

* * * * *